US005801220A

United States Patent [19]
Desai et al.

[11] Patent Number: 5,801,220
[45] Date of Patent: Sep. 1, 1998

[54] RAPIDLY DISINTEGRATING THICKENING COMPOSITION

[75] Inventors: Divyakant S. Desai, West Windsor; Ajit B. Thakur, East Brunswick, both of N.J.

[73] Assignee: E.R. Squibb & Sons, Inc., Princeton, N.J.

[21] Appl. No.: 548,308

[22] Filed: Nov. 1, 1995

[51] Int. Cl.$^6$ .................. D01J 20/26; D01J 20/10; D01J 20/14; D01J 20/16

[52] U.S. Cl. .................. 524/13; 524/28; 524/35; 524/46; 524/442; 524/447; 524/451; 524/791; 424/405; 424/464; 424/465; 424/76.5; 512/4; 252/194; 252/315.1; 252/315.3; 252/315.6; 502/402; 502/404; 502/407; 604/372; 604/373; 604/374

[58] Field of Search .................. 524/13, 28, 35, 524/45, 46, 442, 447, 451, 791; 424/464, 465, 76.5, 76.6, 405; 512/4; 252/194, 184, 315.1, 315.3, 315.6; 502/402, 404, 407; 604/372, 373, 374

[56] References Cited

U.S. PATENT DOCUMENTS 5,171,781 12/1992 Farrar et al. .................. 524/547

*Primary Examiner*—Nathan M. Nutter
*Attorney, Agent, or Firm*—Stuart E. Krieger

[57] ABSTRACT

A rapid disintegrating and dispersing composition for thickening liquid waste into a thixotropic gel comprises a polymeric acrylic resin and a colloid-forming mixture of microcrystalline cellulose and sodium carboxymethylcellulose. Additional ingredients preferably used in making a tableted form of the composition include microcrystalline cellulose per se, polyvinylpolypyrrolidone, magnesium stearate and amorphous silica. The tablet is placed in suitable containment means such as a containment bag. The thixotropic properties of the composition enable the gelled waste to be restored to a liquid when small amounts of hand pressure are applied to the waste containment bag, thereby providing a convenient and simple means for disposal.

12 Claims, No Drawings

RAPIDLY DISINTEGRATING THICKENING COMPOSITION

BACKGROUND OF THE INVENTION

1. Field of the Invention

This invention relates to a rapidly disintegrating composition for thickening bodily fluids, such as liquid wastes excreted from the human body, especially through artificial intestinal and/or urinary passages, or from an incontinent person, or for liquid matter ejected from the stomach, such as vomitus.

2. Description of the Prior Art

An ostomy is a surgical procedure wherein an artificial opening is made through the abdominal wall for the purpose of eliminating waste. In various types of ostomies, such as ileostomy and urostomy, the waste is in a liquid form. Persons who have undergone such surgery become incontinent and require a suitable drainage or collection means such as a pouch or containment bag that must be worn at all times to collect the continuous flow of fluid waste until such time as it is disposed.

The pouch or containment bag generally holds about 600–800 milliliters of waste bodily fluids, such as urine, which needs to be disposed of about 3–4 times a day. Since the contents of the pouch are in a liquid state, splashing or uncontrolled movement of the liquid waste can occur during the various normal daily activities of a person outfitted with a pouch or containment bag, also referred to as an "ostomy bag".

The splashing of liquid waste is undesirable and embarrassing for obvious reasons. In order to ameliorate and control the splashing and movement of such liquid waste, a rapidly disintegrating and dispersing composition that can thicken or immobilize liquid waste into which it comes into contact is highly desirable.

Various thickening compositions and waste collection means have been developed to assist the person who has undergone an ostomy, referred to as an "ostomate". U.S. Pat. No. 4,179,367 to Barthell discloses an agent for thickening the excreted contents of the intestine and/or urine of persons with artificial intestinal and/or urinary passages. The agent contains at least one cross-linked polymer that swells in water. The polymer is based on an acrylic acid derivative. A hydrophilic adsorption agent, such as silicic acid is also included. Barthell's composition takes about 10 minutes to transform the waste products that have collected in a containment bag into a viscous gel.

U.S. Pat. No. 5,116,139 to Young et al discloses a containment and disposal bag for waste fluids that includes a hydrophilic gellable material, comprising a polymer which is water activated to gel rapidly, such as acrylonitrile based polymers. Also included is a material such as a protease enzyme to break down the urine to enhance the operation of the gellable material. Deodorants and fragrances can also be used as well as a biocide or antiviral material.

PCT International Publication No. WO92/10220 to Eastman discloses a flexible and permeable drainage bag for collecting urine from a catheterized or ostomy patient which includes water swellable, water insoluble gel-forming polymer particles, such as cross-linked polyacrylimides.

SUMMARY OF THE INVENTION

A rapid disintegrating and dispersing composition for thickening liquid waste into a thixotropic gel comprises a polymeric acrylic resin and a colloid-forming mixture of microcrystalline cellulose and sodium carboxymethylcellulose. The composition is placed in a containment bag for the collection of the liquid waste which forms a gel upon contacting the composition. The thixotropic properties of the composition enable the gelled waste to be restored into a liquid when small amounts of pressure are applied to the containment bag, thereby affording a convenient and simple means for disposal.

DESCRIPTION OF THE PREFERRED EMBODIMENTS

The present invention comprises a rapidly disintegrating and dispersing composition that can be used to control the splashing or uncontrolled movement of liquid waste that is received and contained in a collecting pouch or containment bag.

The inventive composition comprises a highly absorbent finely divided polymeric acrylic resin and a colloid-forming mixture of microcrystalline cellulose and sodium carboxymethylcellulose as a dispersant.

The polymeric acrylic resin can be formed from polymers based on acrylic acid derivatives, particularly those based on acrylic and methacrylic acid, acrylamide and acrylonitrile.

Cross-linked homopolymers of salts of acrylic acid or methacrylic acid, for example, the alkali metal acrylates and alkali metal methacrylates are suitable, such as the corresponding sodium salts or mixtures or polymers from acrylates and methacrylates.

Also suitable are copolymers of acrylic acid derivatives, acrylic acid, methacrylic acid, acrylamide, methacrylamide and acrylonitrile, either with each other or with vinyl pyrrolidone. Among these, copolymers of acrylic acid and methacrylic acid and copolymers of acrylic acid or methacrylic acid with acrylamide, methacrylamide and acrylonitrile can be used, as well as mixtures of different copolymers.

Examples of cross-linked polymers which may be used in accordance with the invention are:

(1) Homopolymers based on sodium acrylate, sodium methacrylate, acrylamide, and vinyl pyrrolidone.

(2) Copolymers based on sodium acrylate and acrylate acid, sodium acrylate and sodium methacrylate, sodium acrylate and acrylamide, sodium methacrylate and acrylamide, sodium acrylate and acrylonitrile, sodium methacrylate and acrylonitrile, vinyl pyrrolidone and acrylonitrile, and acrylamide and acrylonitrile, especially those containing a major amount by weight of (meth)acrylic acid, amide or nitrile units.

Suitable cross-linking agents for polymers of classes (1) and (2) are olefinic monomers which are at least bifunctional, such as methylene bisacrylamide, divinyl benzene, trisallyl cyanurate, trisallyl phosphate etc., which, relative to the weight of the monomers according to (1) and (2), are used in proportions of about 0.05 to 3.00% by weight, especially in proportions of about 0.1 to 1.0% by weight. The preparation of the corresponding cross-linked polymers by radical or redox polymerization is known.

The polyacrylic resin is most preferably a copolymer of sodium acrylate and acrylic acid, available, for example, under the trade name Salsorb® 90 (Allied Colloids Inc., Suffolk, Va.). Another suitable material is a graft polymer of oxidized starch and acrylonitrile available under the trade name Water-Lock® (Grain Processing Corp.).

The highly absorbent polymeric acrylic resin has a particle size distribution ranging from about 45 to 850 microns and varies from about 50 to 98 weight %, preferably from about 60 to 80 weight %, and most preferably about 65 to 70 weight % of the thickening composition.

The thickening composition also includes a colloid-forming dust-like mixture of finely divided particles of microcrystalline cellulose and sodium carboxymethylcellulose, which functions as a dispersant. The colloid-forming mixture can exist in a ratio of about 80 parts microcrystalline cellulose to about 20 parts of sodium carboxymethylcellulose, preferably about 90 parts microcrystalline cellulose to about 10 parts sodium carboxymethylcellulose, and most preferably about 89 parts microcrystalline cellulose to about 11 parts sodium carboxymethylcellulose, and has a bulk density of about 0.6 grams/cubic centimeter.

The colloidal mixture of microcrystalline cellulose and sodium carboxymethylcellulose is available under the trade name Avicel® RC 591 (FMC Corporation, Philadelphia, Pa.). Other suitable dispersants can also be used and include sodium alginate, tragacanth, methyl cellulose, magnesium aluminum silicate, xanthum gum and sodium carboxymethyl cellulose.

The amount of dispersant can vary from about 2 to 50 weight %, preferably from about 5 to 15 weight % and most preferably about 6 to 10 weight % of the thickening composition.

Liquid waste that contacts the inventive composition forms a gel. The thixotropic properties of the gel facilitates the subsequent drainage and removal of the liquid waste from the containment pouch by the application of slight hand pressure, that is, by squeezing the pouch.

The inventive thickening composition can be prepared for use in the form of finely divided particles, but it is most suitably and preferably provided in a coherent state, such as in the form of a tablet or capsule for simple and convenient placement in the liquid waste containing means, such as the containment bag. The use of the term "tablet" herein is intended to encompass the inventive thickening composition in a cohesive state in any suitable physical form.

After placement of the tableted composition in the containment bag, an important objective of the invention is for the thickening composition to rapidly disintegrate as it comes into contact with the liquid waste. This ability to rapidly disintegrate enables the thickening composition to optimize its gelling action and to control the splashing and movement of the liquid waste entering the containment bag. In essence, the inventive composition substantially immobilizes the liquid waste as it enters the containment bag.

The tableted thickening composition preferably includes polyvinylpolypyrrolidone to enhance its disintegration and dispersion in the containment bag. Polyvinylpolypyrrolidone is available under the trade name Polyplasdone® XL-10 (GAF Chemicals Corporation, Wayne, N.J.).

Other suitable disintegrating substances include croscarmellose sodium (AC-Di-Sol® from FMC Corp.), pregelatinized starch (Starch® 1500 from Colorcon Co. ), sodium starch glycolate (Explotab® from Mendell Co.; Primojel® from Generichem Co.).

The polyvinylpolypyrrolidone and other suitable substances can vary from about 2 to about 10 weight %, preferably about 4 to about 8 weight % and most preferably about 6 to about 7 weight % of the thickening composition.

The thickening composition can also include pharmaceutical grade microcrystalline cellulose per se in the form of spherical particles as a separate and distinct component from the mixture of microcrystalline cellulose and sodium carboxymethycellulose. The microcrystalline cellulose has been found to aid the formation of tablets and has a bulk density of about 0.3 grams/cubic centimeter.

The microcrystalline cellulose is preferably available under the trade name Avicel® PH 102 (FMC Corporation, Philadelphia, Pa.). Other suitable grades of microcrystalline cellulose are available under the trade names Avicel® PH 101, Avicel® PH 103, Avicel® PH 112, Avicel PH 200, Avicel PH 301, and Avicel PH 302, all from FMC Corp., and Emcocel® from Mendell Co.

The microcrystalline cellulose can vary from about 0.5 to about 30 weight %, preferably from about 1 to about 10 weight %, and most preferably from about 1.5 to about 3 weight % of the thickening composition.

In manufacturing the tableted thickening composition, the inclusion of magnesium stearate is also recommended. Magnesium stearate has been found useful as a lubricant component to aid in the tableting operation. Other suitable lubricants include stearic acid, soldium lauryl fumarate, calcium stearate, sodium stearate, and zinc stearate. The magnesium stearate and other suitable lubricants can vary from about 0.05 to about 1.5 weight %, preferably about 0.075 to about 0.15 weight % of the thickening composition.

The rapid disintegration of the tableted composition is also facilitated by the inclusion of amorphous silica. Amorphous silica has been found useful in preventing adhesion between the finely divided particulate components of the tableted composition as it disintegrates when it becomes wet upon contacting the liquid waste. The amorphous silica is preferably available under the trade name Syloid® 244 (W. R. Grace and Company). Other suitable anti-adherent agents include kaolin, talc and calcium silicate.

The amount of amorphous silica and other suitable anti-adherent substances can vary from about 10 to about 30 weight %, preferably from about 15 to about 20 weight %, and most preferably from about 16 to about 18 weight % of the thickening composition.

Additionally, an antimicrobial agent can also be included to prevent microbial growth in the containment bag. Such antimicrobial agents include phenols, aldehydes and quaternary ammonium compounds. The amount of antimicrobial agent can vary from about 1 to about 5 weight %, and preferably from about 2 to about 4 weight % of the thickening composition.

Additionally, perfumes can also be included in the thickening composition to mask undesirable odors which may emanate from the containment bag. Examples of perfumes include synthetic rose oil, synthetic oil of neroli, sandalwood oil and cedar oil. The amount of perfume can vary from about 0.1 to about 1 weight %, preferably from about 0.25 to about 0.75 weight %, and most preferably about 0.4 to about 0.6 weight % of the thickening composition.

A suitable formulation for the thickening composition is as follows:

TABLE 1

| Component | Weight % |
| --- | --- |
| polymeric acrylic resin | 66.68 |
| microcrystalline cellulose and carboxymethylcellulose | 8.00 |
| microcrystalline cellulose per se | 2.00 |
| polyvinylpyrrolidone | 6.66 |

TABLE 1-continued

| Component | Weight % |
| --- | --- |
| magnesium stearate | 0.10 |
| amorphous silica | 16.66 |

EXAMPLE 1

In manufacturing the inventive thickening composition in the form of tablets, a direct compression process is preferably used. All ingredients except magnesium stearate were independently passed through a #20 mesh screen and mixed in a Hobart AS-2000-FDT mixer, for about five minutes to form a blend. Magnesium stearate was screened through a #30 mesh screen and added to the blend which was mixed for an additional three minutes. The final blend was slugged through a Stokes D-3 slugger, using $^{31}/_{32}$ inch tooling. The slugs were then screened through a #20 mesh screen and mixed in the Hobart mixer for three minutes. Additional magnesium stearate was added as needed depending upon the extent that the slugs stuck to the punch and/or dies of the slugger. The blend was then compressed into tablets weighing about 0.4 grams by means of a tablet press.

Tablet hardness was 9.9 Strong Cobb Units (SCU), but can vary from about 6 SCU to about 11 SCU, preferably about 9 SCU to about 10 SCU. Friability was 3%, but can vary from about 0 to 4% when measured on a Roche Friabilator. The disintegrating time, when tablets were added to water, 0.1N hydrochloric acid, or normal saline, was about 15 seconds. Typical disintegrating times can vary from about 8 to 20 seconds, preferably about 12 to 15 seconds.

EXAMPLE 2

To evaluate the physical stability properties, several white round tablets with convex surfaces having the composition of Table 1 were prepared in accordance with Example 1. The tablets had a mean weight of 0.431 grams and a mean thickness of 0.197 inches. The tablets were placed in 95 cubic centimeter high density polyethylene bottles with cotton and a silica gel desiccant. The bottles were induction sealed and placed in storage at 40° C./75% relative humidity (RH) for 22 months. At the end of the storage period, the tablets had a mean hardness of 6.6 SCU, which indicated no significant change from pre-storage tablet hardness. A friability test was also conducted by spinning 20 tablets for 4 minutes in a Roche Friabilator. No loss of weight was evident from the initial weight of the 20 tablets. The tablets were also subjected to a disintegration test by placing them in 50 milliliters of normal saline solution (0.9% NaCl) at ambient conditions. The tablets disintegrated completely and absorbed an average of 25 milliliters of saline per tablet.

EXAMPLE 3

0.5 gram tablets were made using the formulation of Table 1 and the tableting procedure of Example 1. The tablets were found to disintegrate and immobilize 40 milliliters of water in a 50 milliliter beaker in about 10 seconds. Control tablets containing only polymeric acrylic resin did not disintegrate nor immobilize the water after 60 minutes. The inventive thickening formulation immobilized the liquid so completely that no water spilled when the beaker was inverted.

EXAMPLE 4

A 2 gram tablet having the formulation of Table 1 and tableted in accordance with Example 1 immobilized 750 milliliters of water in 20 seconds. When the tableted thickening composition disintegrated, its absorbent force was so strong that not even FD&C Red 40 dye incorporated in the tablet was able to permeate the water. The dye is ordinarily very water soluble and typically capable of spreading almost instantaneously when it contacts water.

EXAMPLE 5

A 2 gram tablet having the formulation of Table 1 and tableted in accordance with Example 1 immobilized incoming water entering a 1,000 milliliter containment bag over a period of 2.5 hours at a rate of 1 milliliter/minute to simulate the discharge rate of urine and feces. It was also observed that the tablet disintegrated and spread uniformly in the containment bag as it immobilized the incoming liquid.

EXAMPLE 6

A 2 gram tablet having the formulation of Table 1 and tableted according to Example 1 was placed in a 1,000 milliliter containment bag. About 900 milliliters water was pumped into the bag at the rate of 82 milliliter/minute. In spite of such a high rate of flow, the tablet thickening composition disintegrated and immobilized the liquid. It was also observed that the thickening composition distributed itself evenly in the bag as it disintegrated. The thixotropic nature of the thickening composition enabled it to fluidize and drain out of the containment bag after the application of gentle hand pressure.

Although this invention has been disclosed in the context of thickening the liquid waste from an ostomy patient, it is also equally applicable to thickening other types of liquid waste, such as urine from an incontinent person, or vomitus. To deal with such situations, the thickening composition can be placed in a suitable containment means, such as the discomfort bags commonly found on airplanes and seagoing vessels. The vomitus contacting the thickening composition will thicken into a gel in about the same manner as the aforementioned liquid waste.

In the case of an incontinent person, suitable containment means equipped with the thickening composition can be fitted to the incontinent person, so that the excreted urine will thicken into a gel for convenient and unobtrusive disposal.

What is claimed is:

1. A method for thickening and disposing of liquid waste selected from the group consisting of waste excreted from an artificial opening through the abdominal wall of an ostomy patient, vomitus, and the liquid waste of an incontinent person, comprising:

(a) placing a rapidly disintegrating thickening composition in a suitable containment means adapted to collect the continuous flow of said liquid waste;

(b) collecting the continuous flow of said liquid waste in the containment means;

(c) contacting the liquid waste as it collects in the containment means with the rapidly disintegrating thickening composition, said thickening agent comprising,
   i) about 50 to 98 weight % of a highly absorbent, finely divided polymeric acrylic resin, and
   ii) about 2 to 50 weight % of a dispersant selected from the group consisting of a mixture of microcrystalline cellulose and sodium carboxymethylcellulose, sodium alginate, tragacanth, methyl cellulose, magnesium aluminum silicate, xanthum gum, sodium carboxymethylcellulose and mixtures thereof;

(d) to thereby form a thixotropic gel as a result of contacting the liquid waste with the thickening composition, and wherein the properties of the thixotropic gel enable it to be restored to a liquid when sufficient amounts of hand pressure are applied to the containment means, to enable the gelled waste to be disposed of in the form of a liquid.

2. The method of claim 1, wherein the thickening composition is in the form of a tablet.

3. The method of claim 2, wherein the thickening composition includes about 0.5 to 30 weight % of microcrystalline cellulose per se.

4. The method of claim 2, wherein the thickening composition includes about 2 to 10 weight % of a thickener selected from the group consisting of polyvinylpolypyrrolidone, croscarmellose sodium, pregelatinized starch, sodium starch glycolate and mixtures thereof.

5. The method of claim 2, wherein the thickening composition includes about 0.05 to 1.5 weight % of a lubricant selected from the group consisting of magnesium stearate, stearic acid, sodium lauryl fumarate, calcium stearate, sodium stearate, zinc stearate and mixtures thereof.

6. The method of claim 2, wherein the thickening composition includes about 10 to 30 weight % of anti-adherent selected from the group consisting of amorphous silica, kaolin, talc, calcium silicate and mixtures thereof.

7. The method of claim 1, wherein the dispersant is a colloid forming mixture of microcrystalline cellulose and sodium carboxy methylcellulose.

8. The method of claim 1, wherein the colloid forming mixture exists in a ratio of about 80 parts microcrystalline cellulose to about 20 parts sodium carboxy methylcellulose.

9. The method of claim 1, wherein the polymeric acrylic resin is based on acrylic acid derivatives selected from the group consisting of acrylic acid, methacrylic acid, acrylamide, acrylonitrile, cross-linked monopolymers of salts of acrylic acid or methacrylic acid, copolymers of acrylic acid derivatives, and mixtures thereof.

10. The method of claim 1, wherein the polyacrylic acid is a copolymer of sodium acrylate and acrylic acid.

11. The method of claim 1, wherein the polymeric acrylic resin varies from about 60 to 80 weight %.

12. The method of claim 1, wherein the colloidal dispersant varies from about 5 to 15 weight %.

* * * * *